United States Patent [19]

Smith

[11] Patent Number: 4,962,212

[45] Date of Patent: Oct. 9, 1990

[54] PROCESS FOR THE PREPARATION OF 2-(2-FURYL)ETHANOL AMINE

[75] Inventor: Lowell R. Smith, Kirkwood, Mo.

[73] Assignee: Monsanto Company, St. Louis, Mo.

[21] Appl. No.: 457,055

[22] Filed: Dec. 26, 1989

[51] Int. Cl.$^5$ .................. C07D 307/14; C07D 307/54
[52] U.S. Cl. .................... 549/491; 544/185; 549/483
[58] Field of Search ............... 549/483, 491; 544/185

[56] References Cited

U.S. PATENT DOCUMENTS 2,400,913  5/1946  Burger ........................... 549/491 X
2,547,712  4/1951  Long et al. ..................... 549/491 X Primary Examiner—Richard L. Raymond
Attorney, Agent, or Firm—William I. Andress

[57] ABSTRACT

The invention disclosed herein relates to a process for producing heterocyclic ethanolamines, especially 2-(2-furyl)ethanolamine.

8 Claims, No Drawings

PROCESS FOR THE PREPARATION OF 2-(2-FURYL)ETHANOL AMINE

FIELD OF THE INVENTION

This invention pertains to the field of processes for producing ethanol amines.

BACKGROUND OF THE INVENTION

Various processes are disclosed in the art for producing a variety of substituted ethanol amines. For example, U.S. Pat. No. 2,400,913 describes a process for producing various heterocyclic tertiary-amino alcohol compounds. Among the heterocyclic tertiary-amine derivatives disclosed in the '913 patent are furyl tertiary amino alcohols. The compounds of the '913 patent are produced by reacting acyl halide derivatives of the heterocyclic compounds, including furan, with a diazoalkane to yield the corresponding diketone. The diketone is treated with a hydrogen halide to form the $\alpha$-halogeno ketones, which, in turn are reacted with secondary amines to yield the corresponding $\alpha$-tertiary amino ketones. Those ketones are then reduced to the corresponding alcohol. While the reduction may be carried out with catalytically-activated hydrogen, in the specific case of compounds in the furan series, the reduction is stated to be more advantageously carried out with an oxidizable metal alkoxide, e.g., aluminum isopropoxide, magnesium ethoxide, and the like.

U.S. Patent 2,547,712 describes a process for producing certain 1-[2-furyl]-2-aminopropane diols. In a more relevant disclosure, in Example 2 of the '712 patent, the compound 2-furyl aminomethyl ketone hydrochloride is produced by reacting a 2-furyl bromomethyl ketone hexamethylene tetraamine complex with HCl. In the next step the 2-furyl aminomethyl ketone is added to a mixture of glacial acetic acid and acetic anhydride to which is then added sodium acetate. The product of that reaction is 2-furyl acetamidomethyl ketone, which is reacted with formalin, sodium bicarbonate and methanol to form 2-furyl-$\alpha$-acetamido-$\beta$-hydroxyethyl ketone. This product was then reduced to the corresponding diol with aluminum isopropoxide (the catalyst of the '913 patent) in isopropanol.

U.S. Pat. No. 4,072,760 discloses another process for producing phenyl-ethanolamines. In one scheme (Column 17) a ketone of a substituted phenyl tertiary amino hydrochloride salt is reduced with a Pd/C catalyst in methanol to the corresponding alcohol. This compound is used to prepare the corresponding compounds of Formula II in '760, which are used to prepare the final products (Formula I) of that patent.

Although it is known to chlorinate methyl ketones, the chlorination of furan derivatives (as in a preliminary step to making chloroacetyl furan as used in the process herein), is a special case. Thus, furan derivatives show extreme susceptibility to acids (Elderfield, Heterocyclic Compounds, J. Wiley and Sons, 1950, pages 161, 170). The HCl co-produced in a chlorination would be expected to decompose the furan ring. This is indicated by the only known process for preparing 2-chloroacetyl furan which is a cumbersome, dangerous synthesis using diazomethane. Election-withdrawing groups, such as NO₂, decrease the sensitivity to acids.

In the preparation of hydrochloride salts of furanamino ketone, by the known Delapine reaction, bromo derivatives are generally used. Accordingly, in the present process, it was found that a tetrabutylammonium bromide catalyst was necessary to catalyze the reaction of 2-chloroacetylfuran with hexamethylenetetraamine to produce the corresponding hydrochloride salt.

Further, the hydrogenation of furan derivatives is not always straight-forward. Elderfield reported that often ring reduction or cleavage occurs. The only reductions in this area are of disubstituted amines only and the reduction is done with an oxidizable metal alkoxide, e.g., aluminum alkoxide, as used in the '913 and '712 patents; such reaction was found not to be operable for a primary amine derivative as herein, but resulted in decomposition.

It is an object of this invention to provide an improved, more efficient and economical process for producing heterocyclic ethanol amines, especially 2-(2furyl)ethanol amine.

The products of this invention are useful as starting materials to produce 5-heterocyclic-substituted oxazolidine compounds, which are useful as antidotes (or "safeners", "antagonistics" or "protectants") to reduce or eliminate the phytotoxicity of herbicides against crop plants, e.g., corn, soybeans, etc. Those said antidotal compounds are publicly known from European Patent Application No. 304,409, published Feb. 22, 1989, and South African Patent No. 5997, issued June 28, 1989.

SUMMARY OF THE INVENTION

The present invention relates to an improved, economical, process for producing compounds useful as precursors to prepare other compounds having important use as antidotes for herbicides.

More particularly, the invention process in general aspects involves a simple sequence of operations, beginning with known and commercially available materials. In summary, the process for this invention involves the preparation of compounds of the formula

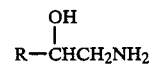
$$R-\overset{OH}{\underset{|}{C}}HCH_2NH_2 \qquad I$$

wherein R represents a 2- or 3-furyl or tetrahydrofuryl radical which may be substituted with a lower alkyl group, which comprises:

(a) reacting a compound of the formula

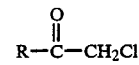
$$R-\overset{O}{\overset{\|}{C}}-CH_2Cl \qquad II$$

with hexamethylenetetraamine and tetrabutylammonium bromide or iodide to produce a compound of the formula.

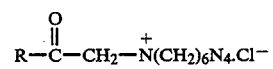
$$R-\overset{O}{\overset{\|}{C}}-CH_2-\overset{+}{N}(CH_2)_6N_4.Cl^- \qquad III$$

(b) reacting the compound of Formula III with an aqueous or alcoholic solution of HCl to form a compound of the formula

$$R-\overset{O}{\overset{\|}{C}}-CH_2NH_2.HCl \quad \text{and} \qquad IV$$

(c) reacting the compound of Formula IV with water or an aqueous alcoholic solution of Raney ® nickel into which solution hydrogen is introduced followed by introduction of an alkaline material and recovering the compound of Formula I.

In a preferred embodiment R in the above formula I is the 2-furyl radical.

DETAILED DESCRIPTION OF THE INVENTION

Example 1

A. Hexamethylene tetraamine (HMTA) salt of 2-chloroacetylfuran.

A solution of 2-acetylfuran (22 g.) in chloroform (80 ml.) was maintained at <35° C. by cooling in an ice bath while chlorine was passed into the solution for one half hour. At this time the glc peaks of acetylfuran and 2-chloroacetylfuran were approximately equal. Air was blown through the solution for 5 min. and hexamethylenetetramine (20 g.) and tetrabutylammonium bromide (4 g.) were added. The solution was stirred for sixteen hours and the resulting solid (41 g.) was filtered. The solid was reslurried with chloroform, filtered and dried giving 30.75 g of product.

B. 2-(2-furyl) aminomethyl hydrochloride.

The above solid (14 g.) was slurried in ethanol (80 ml.) and 36% HCl (20 ml.) was added. The slurry was stirred and heated to 80° C. and cooled. The solid was filtered, slurried with water (5 ml.) and refiltered. The solid was washed with ethanol and dried. This produced 7.0 g. of product.

C. 2-(2-furyl) ethanolamine.

The above solid was dissolved in 80% methanol (80 ml.) and wet Raney® nickel (3 g.) was added. The solution was placed in a Parr shaker and a pressure of 3.5 Kg./sq. cm. of hydrogen was applied. The solution was shaken for nine hours, removed from the shaker and evaporated to dryness. Methylene chloride and dry potassium carbonate were added. The mixture was filtered and the methylene chloride was evaporated leaving a solid shown by glc and pnmr to contain 2-(2-furyl-)ethanolamine.

Example 2

This example illustrates the use of the compound of Example 1 to prepare an important antidotal compound, viz., oxazolidine, 3-(dichloroacetyl)-5-(2-furanyl)-2,2-dimethyl-.

To a clean, dry 22-L flask fitted with overhead stirrer, cooling bath, reflux condenser, nitrogen blanket, vacuum and addition funnel with sub-surface feed is charged 13.5 L acetone and 570 g of 2-(2-furyl)ethanolamine at 20°-25° C. An endotherm of mixing of 2°-3° may occur; the mixture is gently warmed to 20°-25° C. Samples are taken periodically and analyzed by GC until complete conversion to the above oxazolidine product is indicated (alcut 2 hours).

The solution is cooled to 0° C and 506 g triethylamine are added (no exotherm). A total of 697 g of dichloroacetyl chloride (DCAC) is charged to the addition funnel, then DCAC is added subsurface to the solution in a flask at such rate to maintain the temperature between 0°-5° (preferably 0° C.). After all DACA has been added, a sample is taken and analyzed. If complete conversion to the oxazolidine is indicated, the pressure in the flask is reduced to about 150 mm and acetone is stripped at about 13°-15° C. The contents of the flask are stripped to a slurry, then returned to atmospheric pressure and 10 L of distilled water added slowly and the temperature reduced to 15° C. The resulting solid is filtered and washed with water. Dry overnight on the filter, then transfer to a vacuum oven at 25° C. overnight. Yield is about 930–990 g (~80%) of approximately 93–96% oxazolidine.

In similar manner as in Example 1, other heterocyclic ethanol amine compounds analogous to that produced in the example may readily be produced. For example, other analogs of the compound of Example 1 include the 2-(3-furyl)ethanolamine, 2-[2-(5-methylfuranyl)] ethanolamine and the 3- and 4-methylfuranyl isomers thereof and the tetrahydro analogs of the foregoing ethanolamines. It is further within the purview of this invention that alkyl-substituted or unsubstituted thienyl- and pyridinyl ethanolamines be prepared in a manner analogous to that in Example 1.

The reactions in each of the separate steps of the invention process are not dependent upon any critical process parameters. Thus, any suitable inert solvent or carrier may be used in each of Steps A-C. the reaction temperatures, times, pressures, ratios of reactants, etc., are flexible depending upon the raw materials, carriers, final product, etc., as can readily be ascertained by those skilled in the art following the enabling teachings herein.

Thus, by way of non-limiting example, the 2-chloroacetyl furan produced in the initial step in Section A of Example I is a known compound and produced by other means. Also, in that initial step other inert solvents, e.g., carbon tetrachloride may be used in place of the exemplified chloroform.

Further, in Sections B and C of Example 1, where ethanol and methanol, respectively, were used, it is clearly suitable to substitute another alcohol such as propanol, isopropanol, butyl alcohol, amyl alcohol and the like. With further regard to Step C, it has been found more advantageous to use water alone as the media for the Raney-nickel catalyzed hydrogenation, although as exemplified, a methanolic solution is satisfactory. While the hydrogenation catalyst itself was illustrated in Step C with Raney nickel, one may also use other operable catalysts. However, some hydrogenation catalysts are unsuitable in this process, e.g., palladium. Moreover, other reducing agents than hydrogen, e.g., sodium borohydride may be used. Moreover, where in Step C in Example 1 potassium carbonate was the exemplified alkaline material, any strong base may suitably be used, e.g., NaOH, triethylamine, etc.

I claim:

1. Process for preparation of compounds of the formula

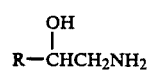 I wherein R represents a 2- or 3-furyl or tetrahydrofuryl radical which may be substituted with a lower alkyl group, which comprises:

(a) reacting a compound of the formula with hexamethylene tetraamine and tetrabutylammonium bromide or iodide to produce a compound of the formula $$R-\overset{O}{\underset{\|}{C}}-CH_2-\overset{+}{N}(CH_2)_6N_4.Cl^-; \quad III$$

(b) reacting the compound of Formula III with an alcoholic solution of HCl to form a compound of the formula $$R-\overset{O}{\underset{\|}{C}}-CH_2NH_2.HCl \quad \text{and} \quad IV$$

(c) reacting the compound of Formula IV with water or an aqueous alcoholic solution of Raney nickel into which solution hydrogen is introduced followed by introduction of an alkaline material and recovering the compound of Formula I.

2. Process according to claim 1 wherein R is the 2-furyl radical.

3. Process for the preparation of 2-(2-furyl)ethanolamine which comprises:
 (a) reacting 2-chloroacetylfuran with hexamethylene tetraamine and tetrabutyl ammonium bromide to obtain the hexamethylene tetraamine hydrochloride salt of 2-chloroacetylfuran;
 (b) reacting the product of Step (a) in an ethanolic solution containing HCl to obtain 2-(2-furyl)aminomethylketone hydrochloride, and
 (c) reacting the product of Step (b) with hydrogen and Raney ® Nickel in admixture with water or an aqueous solution of methanol followed by addition of an alkaline reagent and recovering 2-(2-furyl)ethanolamine.

4. Process according to claim 3 wherein the hydrogenation reaction of Step (c) is conducted at elevated pressure.

5. Process according to claim 4 wherein said alkaline material is an alkali metal hydroxide or carbonate.

6. Process according to claim 5 wherein said alkaline material is NaOH.

7. Process according to claim 5 wherein said alkaline material is $KCO_3$.

8. Process according to either of claims 1 or 3 wherein the 2-chloroacetylfuran starting material in Step (a) is produced by the chlorination of acetylfuran in a suitable solvent.

* * * * *